United States Patent [19]

Isaac

[11] 3,956,491

[45] May 11, 1976

[54] MEDICINE CONTAINING THE MAIN SAPOGENIN OF HELLEBORUS

[75] Inventor: Otto Isaac, Bruchköbel, Germany

[73] Assignee: Deutsche Gold- und Silber-Scheideanstalt vormals Roessler, Germany

[22] Filed: Apr. 7, 1975

[21] Appl. No.: 565,697

[30] Foreign Application Priority Data

Apr. 8, 1974 Germany.............................. 2416978

[52] U.S. Cl.................................... 424/241; 195/4; 260/239.55 A

[51] Int. Cl.²......................................... A61K 31/58

[58] Field of Search............. 424/241; 260/239.55 A

[56] References Cited

FOREIGN PATENTS OR APPLICATIONS 23,66M    3/1964    France............................... 424/241

Primary Examiner—Ethel G. Love
Attorney, Agent, or Firm—Cushman, Darby & Cushman

[57] ABSTRACT

The main sapogenin of the roots and rhizomes of Helleborus species is used in medicine, especially to treat ulcers.

9 Claims, No Drawings

MEDICINE CONTAINING THE MAIN SAPOGENIN OF HELLEBORUS

The roots and rhizomes of Helleborus species contain a saponin mixture whose main sapogenin has the structure of a spiro-5,25(27)-diene-1β,3β,11α-triol (formula I)

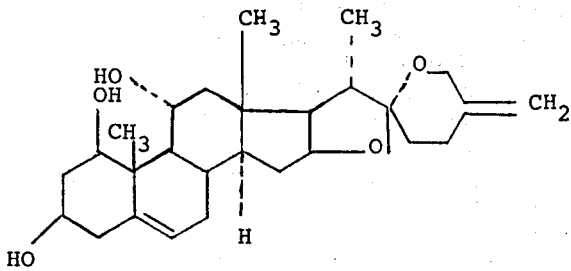

I

According to Linde, Helv. Chim. Acta Vol. 54, pages 1703–1708 with specific reference to page 1707, to recover this sapogenin rhizomes and coarsely pulverized roots of Helleborus species are taken up in water and left to an autofermentation for 22 days. Subsequently, the drug residue is filtered off and extracted with aqueous alcohol. The residue of the alcoholic extract is chromatographed on silica gel. The sapogenin fraction is recrystallized from methanol-acetone. By preparative thin layer chromatography in the system diisopropylether-ethanol (92:8 by volume) there is finally obtained the pure sapogenin, M.P. 236°–240°C. In the specific example in Linde employed Helleborus odorus but mention is made that Helleborus niger was also used in similar manner to obtain the same sapogenin of formula I. The entire disclosure of Linde is incorporated herein by reference and relied upon.

Rhizomes are underground, more or less thickened axis of the shoot which plainly differs from roots through the presence of mostly scaly leaves and through their organization. Webster's Seventh New Collegiate Dictionary defines rhizome as "a somewhat elongate usually horizontal subterranean plant stem that is often thickened by deposits of reserve food material, produces shoots above and roots below, and is distinguished from a true root in possessing buds, nodes, and usually scalelike leaves."

This main genin of the sapogenin mixture which is contained in the roots and rhizomes of Helleborus species can be recovered if the roots and rhizomes of Helleborus species or drugs or extracts obtained therefrom are treated with cellulase.

The treatment with the cellulase can be carried out in accordance with German Application P 24 16 979.7 or my corresponding U.S. application Ser. No. 565,698 entitled "Process for Recovering the Main Sapogenins from the Roots and Rhizomes of Helleborus," filed on even date. The entire disclosure of said United States application is hereby incorporated by reference and relied upon. In place of cellulase there can also be employed hemicellulase or β-glucosidase as noted in said United States application.

The enzyme treatment with the cellulase takes place in a customary manner. There is suitably maintained a temperature between 20° and 50°C. A temperature between 30° and 40°C. is generally especially favorable.

According to the process of the invention there can be employed directly the pulverized roots and rhizomes of Helleborus species or there can be used an extract recovered in customary manner or a drug from Helleborus species which has been worked up and pulverized in customary manner. The treatment can be carried out in solution, in suspension or in form of a mash. Thus, for example, the enzyme can be added to the autolysate of roots and rhizomes of Helleborus species.

However, it is also possible to first produce an extract in kwown manner from the roots and rhizomes or a drug produced therefrom and treat this, in a given case after a conventional purification, with the enzyme, i.e. cellulase (or hemicellulase or β-glucosidase. For this purpose suitably the roots or rhizomes or drug first is extracted with alcohol (ethyl alcohol) or an alcohol water mixture e.g. containing a maximum of 50% water. The thus obtained extract is subsequently extracted by shaking with organic solvents, e.g. water immiscible organic solvents, for example, aromatic hydrocarbons, e.g. benzene, toluene, xylene, halohydrocarbons, e.g. chloroform, carbon tetrachloride, 1,2-dichloroethane, or halo-hydrocarbon-alcohol mixtures as for example chloroform-ethanol. If halohydrocarbon-alcohol mixtures are used the mixing ratio is preferably the mixing ratio is preferably 2:1. However, it is favorable if the organic extract obtained is preliminarily purified.

Such a preliminary purification can take place in customary manners therefore. However, it can also take place for example by chromatographization of a silica gel whereby as silica gel there is used a synthetically produced highly porous, amorphous, silica in the form of hard particles with a particle size of 0.15 to 10 mm. Especially favorable is a particle size of 0.15 to 0.30 mm. The water content of this silica, for example, can amount to 10%. The specific surface area can be from 300 m²/g to 650 m²/g. Generally the surface area is about 400 m²/g. The apparent density can be from 400 to 750 g/l. An apparent density (bulk density) of 450 to 500 g/l is propitious.

As eluting agents for the silica chromatography of the organic extracts of the roots and rhizomes of Helleborus species there may be mentioned aliphatic halohydrocarbons, e.g. methylene chloride, chloroform, carbon tetrachloride, 1,2-dichloroethane, trichloroethylene, ethylene dibromide, ethylene tetrachloride, mixtures of aliphatic halohydrocarbons (e.g. those juust mentioned) with aliphatic alcohols, e.g. alkanols such as methanol, ethanol, propanol, isopropanol or butanol, esters of aliphatic acids with aliphatic alcohols, e.g. methyl acetate ethyl acetate, butyl acetate, ethyl propionate, ethyl formate, methyl butyrate, ester-alcohol mixtures (such as mixtures of the above-mentioned carboxylic acid esters and alcohols), ester-alcohol-water mixtures (such as mixtures of the above-mentioned carboxylic acid esters and alcohols with water, benzene, halobenzenes, e.g. chlorobenzene, fluorobenzene, bromobenzene and o-dichlorobenzene, alkyl benzenes, e.g. toluene, o-xylene, m-xylene, p-xylene, ethyl benzene and cumene, alkyl benzene-alcohol mixtures (such as mixtures of the above-mentioned alkyl benzenes and alcohols, ester-pyridine mixtures (such as mixtures of the above-mentioned carboxylic acid esters with pyridine), halohydrocarbon-pyridine mixtures (such as mixtures of the above-mentioned halohydrocarbons with pyridine), halohydrocarbon-alcohol-pyridine mixtures (such as mixtures of the above-mentioned halohydrocarbons and alcohols with pyridine), ester-pyridine-water mixtures (such as mixtures of the above-mentioned carboxylic acid esters with pyridine and water), mixtures of benzene, halobenzenes and alkylbenzenes with pyridine (such as mixtures of benzene, the above-mentioned halobenzenes and the above-mentioned alkylbenzenes with pyrdine), aliphatic ketones, e.g. acetone, methyl ethyl ketone and methyl butyl ketone, ketone-water mixtures (such as mixtures of the abovementioned ketone with water, ketone-benzene mixtures (such as mixtures of the above-mentioned ketones with benzene, ketone-benzene-glacial acetic acid mixtures (such as mixtures of the above-mentioned ketones with benzene and acetic acid), etc. It is understood that other mixtures of the above-mentioned types of components are also possible. The optimum ratio of mixing the components can be readily ascertained in a separate preliminary test.

For example as the above-mentioned aliphatic liquids there can be usedthe lower molecular weight liquids which are customarily used as solvents. The term halogen means fluorine, chlorine and bromine, preferably fluorine and chlorine. Under alkyl benzene these are included with lower alkyl groups. Examples are toluene, ethyl benzene, xylene and the others mentioned supra.

The prepurified and completely solvent-free saponin fraction is then incubated in water with the cellulase (or hemicellulase or $\beta$-glucosidase). The incubation can be carried out for example at a temperature of 20° to 50°C.

There can be used in the process of the invention the commercial cellulase (or hemicellulase or $\beta$-glucosidase) preparatives. Likewise, there can be used preparatives of the just named enzymes which have been produced according to known processes for such purpose form fungi, microorganisms (trichodermo viride, for example), protozoa, bacteria, insects, plants or invertebrate animals such as snails (edible snails) and worms (see Sumner et al, The Enzymes, Vol. 1, Part 2 (1951) pages 729–731, the entire disclosure of which is hereby incorporated by reference and relied upon) and Ullmanns Enzyklopadie der technischen Chemie, 3rd edition (1956) pages 391–396, the entire disclosure of which is hereby incorporated by reference and relied upon).

Examples of sources of cellulase include for example barley malt, potato sprouts, aspergillus oryzae, aspergillus niger, merulius lacrymans, myrothecium verrucaria, cellobacillus, cytophaga sp., plectriodium cellulolyticum, eudiplodinium neglectum, trichomonas termopsidis, helix pomatia, bankia setacea, reticulitermes flaipes, termopsis angusticollis, cryptocercus punctulatus and stromatium fulvum.

The enzyme, as for example cellulase, is obtained if the culture medium or the aqueous myceltial extract of fungi is precipitated with alcohol (ethanol), acetone or salt. The crude cellulase can then be further purified, for example, on aluminum oxide. There should be used the freshest possible preparative which has not been stored for long. Stored preparatives should be kept cool and dry. Especially suitable are cellulase preparatives or enzyme concentrates or fungi or Aspergillus species such as *Aspergillus niger, Aspergillus oryzae, Aspergillus flavus, Aspergillus fumigatus, Aspergillus nidulans*. Especially favorable are preparatives or enzyme concentrates from *Aspergillus niger*.

It is necessary by preliminary tests to determine the activity of the cellulase (or other enzyme) and to ascertain the optimum reaction ratios and proportions in the conventional. Enzyme concentrates which consists, for example chiefly of cellulase and hemicellulase appear especially favorable. Frequently, such preparatives contain besides related enzymes such as pectinase, amylase, acid protease, xylanase cellobiase, glucoamylase, endopeptidases, lipase, pectinxylopolygalacturonase. It is likewise favorable if the enzyme preparatives according to the invention contain besides maceraingly acting enzymes (for example pectinglycosidase).

Generally, the enzymatic reaction with the cellulase is ended after 2 days. With enzymes having higher activity, the reaction can be ended even earlier with cellulases having lower activity, however, the treatment can be carried our for a considerably longer time.

The cellulase (or hemicellulase or $\beta$-glucosidase) can be mixed either as such or in aqueous solution with the substrate.

The optimum pH value for the enzyme treatment is about 4.5 to 4.7. It is advantageous to stir the incubate or to keep it in motion in other ways.

The amount in which the cellulase (or hemicellulase or $\beta$-glucosidase) is added depends on the activity of the cellulase (or other enzyme) and also on the substrate used. The cellulase (or other enzyme), for example, can be added in very large excess. If, for example, a crude saponin fraction is added which, for example, is preliminarily purified in the manner given above, there can be added 5 to 100% of the cellulase (or other enzyme) preparative necessary according to the degree of purity determined by thin layer chromatography. If, for example, the drug is directly reacted or roots and rhizomes of Helleborus species then an amount between 1 and 10% based on the drug or the roots and rhizomes is sufficient.

The crude sapogenin resulting from the enzyme treatment can be further worked up according to the customary processes described in the literature. For example, there can be used the process of Linde set forth on page 1707 of the Linde article in Helv. Chim. Acta. Vol. 54 set forth previously. (Chromatograph on $SiO_2$ having a particle size of 0.05 to 0.2 mm).

However, especially desirable is a purification (for example by chromatography) of the crude sapogenin obtained with the help of silica gel with a particle size of 0.2 to 0.5 mm. As elevation agents there are especially suitable lower halogenated hydrocarbons such as methylene chloride and chloroform to which there can be added 1% on up of a lower aliphatic alcohol such as methanol or ethanol.

The thus obtained sapogenin can be recrystallized once from propanol water.

It is possible according to the cellulase (or hemicellulase or $\beta$-glucosidase) process to isolate the Helleborus sapogenin in considerable greater amount than is possible by preparative thin layer chromatography.

As starting materials there can be used the known Helleborus species, for example *Helleborus foetidus L., Helleborus multifidus Vis., Helleborus niger L., Helleborus odorus Waldst.* et *Kit., Helleborus orientalis Lam., Helleborus purpurascens Waldst.* and *Kit., Helleborus veridis.*

Nothing was previously known of the physiological activity of the main sapogen from the roots and rhizomes of Helleborus species. It has now likewise been found that the amin genin recovered from Helleborussaponin has an ulcer healing activity. Furthermore a muscle relaxing and central nervous system influencing activity has been established. The ulcer protective activity can be seen from the following ta table.

| DAILY DOSAGE | ULCER PROTECTING EFFECT |
|---|---|
| 50 mg/kg | 58% |
| 100 mg/kg | 78% |
| 200 mg/kg | 80% |

These tests were carried out according to the method of John and Adrian modified by Wilhelmi on the indometacin ulcer of rats (see Arzeimittelforschung Vol. 19 (1969) pages 45 et seq.).

The determination is carried out in the following manner.

Albino rats of the strain SIV 50 (S. Ivanovas, Kisslegg/allgau) having an initial weight of 250 to 300 grams were held in controlled temperature rooms at 20° to 22°C. in wire cages (Ebeco, Type 3 double width) on a standard diet (Altromin). After 48 hour feeding intervals the animals received 20 mg/kg rat of indometacin in 1.5% tragacanth (1 ml tragacanth solution per 100 grams of rat) applied introgastrally.

One hour after giving the indometacin there was dispensed orally to the animals the test substance. The rats remain otherwise fasting (water ad libitum)

Twenty four hours after giving the indometacin the animals were killed with $CO_1$. The stomach was resected, opened along the great curvature and washed under flowing water.

The ulcerative changes appear as dark, point or stria shaped spots on the mucosa. The evaluation was done according to the method of Munchow Arneimittedforschung Vol. 4 (1954) pages 341–344.

The compound of the invention is suited for the production of pharmaceutical compositions. The medicines contain as the active material the compound of the invention, in a given case in admixture with other pharmaceutically effective materials. The production of the medicine can take place with the use of known and customary pharmaceutical assistants, carriers and diluents.

Such carriers and assistants include for example those recommended in the following literature as adjuvants for pharmacy, cosmetic and related fields such as in Ullmann's Encyklopadie der technischer Chemie, Vol. 4 (1953), pages 1 to 39; Journal of Pharmaceutical Sciences, Vol. 52 (1963), pages 918 et seq.; H. V. Czetsch-Lindewald, Hilfstoffe fur Pharmazie and angrenzende Gebiete; Pharm. Ind. Vol. 2 (1961), pages 72 et seq.; Dr. H. P. Fiedler, Lexicon der Hilfstoffe fur Pharmazie, Kosmetik und angrenzende Gebiete, Cantor Kg. Aulendorf i. Wurtt, 1971.

Examples of such materials include gelatin, natural sugars such as sucrose or lactose, lecithin, pectin, starch (for example corn starch), tylose, methyl cellulose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols, (for example, methyl hydroxypropyl cellulose, methyl cellulose, hydroxyethyl cellulose), stearates, e.g., methylstearate, and glyceryl stearate, magnesium and calcium salts of fatty acids with 12 to 22 carbon atoms, especially saturated acids (for example calcium stearate, calcium laurate, magnesium oleates, calcium palmitate, calcium behenate and magnesium stearate), emulsifiers, oils and fats, especially of plant origin (for example, peanut oil, castor oil, olive oil, sesame oil, cottonseed oil, corn oil, mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compaticle mono- or polyvalent alcohols and polyglycols such as glycerine, mannitol, sorbitol, pentaerythritol, ethyl alcohol, diethylene glycol, triethylene glycol, ethylene glycol, propylene glycol dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono- (1 to 20 carbon atoms alkanols) or polyhydric alcohols such as glycols, glycerine, diethylene glycol, pentaerythritol, sorbitol, mannitol, ethyl alcohol, butyl alcohol, actadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, glycol furfural, dimethyl acetamide, lactamide, lactates, e.g., ethyl lactate, ethyl carbonate, silicones (especially middle viscosity dimethyl polysiloxane) and the like.

For the production of solutions there can be used water or physiologically compatible organic solvents, as for example, ethanol, 1,2-propylene glycol, polyglycols, e.g. diethylene glycol, triethylene glycol and dipropylene glycol and their derivatives, dimethyl sulfoxide, fatty alcohols, e.g. stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g. monoacetic diacetin, glyceryl monostearate, glyceryl distearate, glyceryl monopalmitate, paraffins and the like.

In the production of the preparations there can be used known and conventional solvent aids. As solvent aids there can be used, for example, polyoxyethylated fats, e.g. polyoxyethylated oleo triglyceride, linolized oleo-triglyceride. Examples of oleotriglycerides are olive oil, peanut oil, castor oil, sesame oil, cottonseed oil, corn oil (see also Dr. H. P. Fiedler, "Lexikon der Hilfsstoffe fur Pharmazie, Kosmetik und angrenzende Gebiete", 1971, pages 191 to 195.

Polyoxyethylated means that the materials in question contain polyoxyethylene chains whose degree of polymerization is generally between 2 and 40 and especially between 10 and 20. Such materials can be obtained for example by reaction of the corresponding glyceride with ethylene oxide (for example 40 moles of ethylene oxide per mole of glyceride).

Furthermore, there can be added preservatives, stabilizers, buffers, taste correctives, antioxidants and complex formers (for example ethylendiamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value.

As antioxidants there can be used for example sodium meta bisulfite, ascorbic acid, gallic acid, alkyl gallates, e.g. methyl gallate and ethyl gallate, butyl hydroxyanisole, nordihydrogauraretic acid, tocopherols such as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester benzoic acid), socium benzoate, trichloroisobutyl alcohol, phenol, cresol, benzethonium chloride and formalin derivatives).

The pharmacological and galenical treatment of the compounds of the invetion takes place according to the usual standard methods. For example, the active material or materials and assistants or carriers are well mixed by stirring or homogenization (for example by means of a colloid mill or ball mill), wherein the operation is generally carried out at temperatures between 20° and 80°C, preferably 20° to 50°C.

The drugs can be used for example orally, parenterally, rectally, vaginally, perlingually or locally.

It is also possible to add other medicines.

The compounds of the invention show a good antiulcer activity, for example in indometacin ulcers of rats as well as histamine ulcers of guinea pigs.

The testing of the histamine type of ulcer of guinea pigs is carried out for example by the method of Eagleton and Watt (Peptic Ulcer, Pfeiffer, Munksgaard, Copenhagen, printed in Denmark by Aarhuus, Stiftsbogtrykkerie A/S Arhus ISBN 8716003225 pages 34–44). The entire disclosure of the Eagleton and Watt article is hereby incorporated by reference and relied upon. There were employed predominantly male guinea pigs weighing 300 to 400 grams and the test substance was applied orally after 24 hour feeding intervals and 12 hours deprivation of drinking water. One hour after giving the substance the guinea pigs were given the injection of histamine diphosphate (histamine acid phosphate) at a dosage of 5 mg/kg (the histamine diphosphate was employed in aqueous solution at a concentration of 1 mg histamine disphosphate/ml). The histamine diphosphate was injected introperitoneally. Three hours after the injection of histamine the animals were killed with $CO_2$. The stomachs were resected and cut open along the small curvature and turned upside down over the examination finger. The ulcers were evaluated according to Munchow (Arzneimittelforschung Vol. 4 (1954) pages 341–344).

The calculated control index must in in the order of magnitude between 5 and 15.

The antiulcer activity is comparable to the activity of the known medicine Biogastrone.

The lowest effective dosage in the above mentioned animal experiments for example is 50 mg/kg orally.

As a general dosage range for the above mentioned activity (animal experiments as above set forth) there can be employed for example 50 to 500 mg/kg orally.

The compound of the invention can be used in treating ulcers ventriculi, Ulcus duodeni, gastritis, duodenitis, etc.

The pharmaceutical preparations generally contain between 1 and 50% of the active component of the invention although this can be varied.

The medicine containing the compound can be dispersed in the form of tablets, capsules, dragees or in liquid form. As liquid forms there can be used for example oily or alcoholic solutions as well as emulsions. The preferred forms of use are tablets which contain between 50 and 500 mg of the compound of Formula I or solutions which contain between 0.5 and 10% of the active substance of Formula I.

The individual dosages of the active component of the invention can be between 50 and 500 mg in orally administered medicines.

For example it is recommended to use 1 to 5 tablets containing 50 to 500 mg of active substance three times a day.

The acute toxicity of the compound of the invention in the mouse (expressed by LD50 mg/kg; method of Miller and Tainter; Proc. Soc. Exper. Biol. a. Med. Vol 57 (1944) pages 261 et seq.) on oral application, for example is above 6000 mg/kg.

Unless otherwise indicated all parts and percentages are by weight.

EXAMPLE 1 (TABLETS)

50 grams of Helleborus main sapogenin (Formula I) were mixed with 50 grams of highly dispersed silica, 10 grams of corn starch, and 120 grams of lactose. The powder was granulated with a solution of 5 grams of methyl hydroxypropyl cellulose in about 160 ml of 30% ethanol, the dried granulate mixed with 21 grams of corn starch, 18 grams of talc, 125 grams of microcrystalline cellulose and 1 gram of magnesium stearate and then pressed into tablets in known manner.

One tablet having a weight of 500 mg contained 50 mg of sapogenin.

The Helleborus-main sapogenin (Formula I) was obtained as follows:

100 kg of roots and rhizomes of *Helleborus viridis* were comminuted, defatted with petroleum ether and subsequently exhaustively extracted with 80% aqueous ethanol. The residue of the ethanol extract was taken up in water and the solution extracted by shaking with chlorogform/ethanol (2:1 by volume). The chloroform solution portion was chromatographed on a silica gel column with chloroform/methanol (9:1 by volume) and the fractions examined thin layer chromatographically.

Adsorbent: silica gel for thin layer chromatography
Flowing agent: chloroform/methanol/water (35:25:10 by volume)
Detection: anisaldehyde/sulfuric acid/acetic acid (1:1:100 by volume)

The fractions were collected which essentially contained a brown colored material of average Rf-value (about 0.50) which is localized in the chromatogram between desglucohellebrin and hellebrin.

The residue of the combined fractions (2621 grams) was dissolved under reflux in 2.4 liters of methanol and 2.4 liters of water. After addition of 24 liters of tap water there was distilled off from the solution 4.8 liters of solvent.

After cooling, the solution was treated with 240 grams of a commercial cellulase (Rohm and Haas) as well as 100 ml of toluene and aged at 40°C with occasional shaking. After about 48 hours the reaction was complete. The precipitate was filtered off with suction, washed with hot water and dried. Yield 1100 grams.

The dried precipitate was dissolved in methanol and dichloromethane (50:50 by volume) and the solution chromatographized with dichloromethane/methanol (increasing methanol concentration) on silica gel for column chromatography with a particle size of 0.2–0.5 mm.

The sapogenin fraction (736 grams) was dissolved in 5 liters of n-propanol and the solution treated with 30 liters of water. After 24 hours the crystals which separated were washed with propanol/water and dried.

Formula: $C_{27}H_{40}O_5$
M.P. 238-240°C
$[\alpha]_D^{20} = 86.93°C$ (c = 1.1: pyridine).

EXAMPLE 2 (GELATIN CAPSULES)

500 grams of dimethyl polysiloxane having a viscosity of 360–380 cps at 20°C (Silikonol AK 350) were ground with 20 grams of highly dispersed silica. The grindings were worked into a homogeneous paste on the water both with 130 grams of isopropyl myristimate, 150 grams of a molten mixture of mono, di and triglycerides of saturated fatty acids $C_{12}H_{24}O_2$ — $C_{18}H_{36}O_2$ (i.e. glycerides of a mixture of lauric acid, myristic acid, palmetic acid and stearic acid) which is available in commerce under the designation hard fat (Deutsches Arzneibuch 7th edition) and 200 grams of the Helleborus main sapogenin.

The paste was filled into gelatin capsules in individual dosages of 500 mg. One gelatin capsule contains 100 mg of sapogenin.

EXAMPLE 3 (COATED TABLETS, DRAGEES)

Tablets or dragee nuclei which were produced according to Example I were provided with a coating in known manner of a stomach or small intestine soluble film coat which can consist of for example, suitable cellulose derivatives or other polymeric film formers and suitable additives such as plasticizers, dyes, flavorings, etc. or with suitable dragee coatings.

EXAMPLE 4 (ALCOHOLIC SOLUTION)

7.5 grams of Helleborus-main sapogenin were dissolved in 96% ethanol with 0.5 grams of cherry flavor and the solution filled up to 100 ml with ethanol. For peroral use, 1 ml of the solution is mixed with about 50 to 100 ml of a liquid, e.g. water. 1 ml of the solution contains 75 mg of sapogenin.

The drug can be used in human medicine or in veterinary medicine, e.g. to treat cats, dogs, horses, sheep, cattle, goats, pigs, rats, rabbits and guinea pigs.

The composition of the invention can comprise, consist essentially of or consist of the stated materials and the process can comprise, consist essentially of or consist of the steps set forth.

What is claimed is:

1. A pharmaceutical composition useful in the treatment of ulcers comprising an effective amount of the main sapogenin of the roots and rhizomes of Helleborus species and a non-toxic pharmaceutically acceptable carrier, said sapogenin having the formula

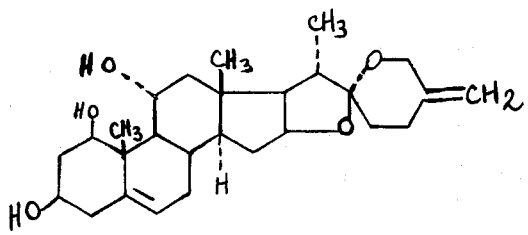

2. A pharmaceutical composition according to claim 1 in the form of a tablet, dragee or capsule.

3. A pharmaceutical composition according to claim 2 in the form of a tablet.

4. A pharmaceutical composition according to claim 2 in the form of a gelatin capsule.

5. A process of treating an ulcer to heal the ulcer in a mammal comprising administering to the mammal an effective amount of the sapogenin composition of claim 1 to heal the ulcer.

6. The process of claim 5 wherein the composition is administered orally, parenterally, rectally, vaginally, perlinqually or locally.

7. The process of claim 6 wherein the composition is administered orally.

8. The process according to claim 7 wherein the composition is administered in a dosage 50 to 500 mg of the sapogenin per kilogram of body weight.

9. The process of claim 5 wherein the ulcer treated is in the stomach or small intestine.

* * * * *